(12) United States Patent
Biedermann et al.

(10) Patent No.: US 8,419,773 B2
(45) Date of Patent: Apr. 16, 2013

(54) STABILIZATION DEVICE FOR STABILIZING BONES OF A VERTEBRA AND ROD CONNECTOR USED THEREFOR

(75) Inventors: Lutz Biedermann, Villingen (DE); Wilfried Matthis, Weisweil (DE)

(73) Assignee: Bierdermann Technologies GmbH & Co. KG, Donaueschingen (DE)

( * ) Notice: Subject to any disclaimer, the term of this patent is extended or adjusted under 35 U.S.C. 154(b) by 740 days.

(21) Appl. No.: 12/035,386

(22) Filed: Feb. 21, 2008

(65) Prior Publication Data

US 2008/0215095 A1    Sep. 4, 2008

Related U.S. Application Data

(60) Provisional application No. 60/903,134, filed on Feb. 23, 2007.

(30) Foreign Application Priority Data

Feb. 23, 2007 (EP) .................................. 07003788

(51) Int. Cl.
*A61B 17/70* (2006.01)

(52) U.S. Cl.
USPC ............................ 606/260; 606/259; 606/278

(58) Field of Classification Search .......... 606/250–260, 606/264–265, 278, 246
See application file for complete search history.

(56) References Cited

U.S. PATENT DOCUMENTS

| 5,360,431 | A | 11/1994 | Puno et al. |
| 5,643,260 | A | 7/1997 | Doherty |
| 5,649,926 | A | 7/1997 | Howland |
| 6,117,137 | A | 9/2000 | Halm et al. |
| 6,224,598 | B1 | 5/2001 | Jackson |
| 6,478,797 | B1 | 11/2002 | Paul |
| 6,652,526 | B1 | 11/2003 | Arafiles |
| 6,783,527 | B2 | 8/2004 | Drewry et al. |
| 6,896,677 | B1 | 5/2005 | Lin |

(Continued)

FOREIGN PATENT DOCUMENTS

| CA | 2 577 436 A1 | 6/2006 |
| DE | 39 27 782 A1 | 2/1991 |

(Continued)

OTHER PUBLICATIONS

Clean set of claims from Amendment filed Mar. 15, 2011 for U.S. Appl. No. 11/512,461, 5 sheets.

(Continued)

*Primary Examiner* — Eduardo C Robert
*Assistant Examiner* — Christina NegrelliRodriguez
(74) *Attorney, Agent, or Firm* — Christie, Parker & Hale, LLP

(57) ABSTRACT

A stabilization device for stabilizing bones of a vertebra includes a first rod, a second rod, a rod connector connecting the first rod and the second rod, the rod connector comprising a receiving portion for receiving the first rod and a fixation element for fixing the first rod in the receiving portion, wherein in the receiving portion a rod contacting surface is provided and wherein the contour of this rod contacting surface has deviations from the contour of the surface of the first rod. The rod connector allows to connect a flexible rod, for example made of an elastomer material, with a rigid rod, made for example of a metal.

25 Claims, 8 Drawing Sheets

U.S. PATENT DOCUMENTS

| | | | |
|---|---|---|---|
| 2003/0045878 A1 | 3/2003 | Petit et al. | |
| 2003/0083657 A1 | 5/2003 | Drewry et al. | |
| 2003/0220642 A1 | 11/2003 | Freudiger | |
| 2004/0116928 A1 | 6/2004 | Young et al. | |
| 2005/0096659 A1 | 5/2005 | Freudiger | |
| 2005/0143737 A1 | 6/2005 | Pafford et al. | |
| 2005/0203518 A1 | 9/2005 | Biedermann et al. | |
| 2005/0228378 A1* | 10/2005 | Kalfas et al. | 606/61 |
| 2005/0277932 A1* | 12/2005 | Farris | 606/61 |
| 2006/0064092 A1 | 3/2006 | Howland | |
| 2006/0241602 A1 | 10/2006 | Jackson | |
| 2007/0005063 A1 | 1/2007 | Bruneau et al. | |
| 2007/0093820 A1 | 4/2007 | Freudiger | |
| 2007/0173825 A1 | 7/2007 | Sharifi-Mehr et al. | |
| 2008/0114404 A1* | 5/2008 | Matthis et al. | 606/309 |
| 2008/0234743 A1* | 9/2008 | Marik | 606/257 |

FOREIGN PATENT DOCUMENTS

| | | |
|---|---|---|
| EP | 1 719 468 A1 | 11/2006 |
| JP | 2005-169071 | 6/2005 |
| WO | WO 2005/046515 A2 | 5/2005 |
| WO | WO 2005/099603 A1 | 10/2005 |

OTHER PUBLICATIONS

Office action dated Jun. 21, 2011 for U.S. Appl. No. 11/512,461, 9 sheets.
Clean set of claims from Amendment After Final filed May 9, 2011 for U.S. Appl. No. 11/854,508, 5 sheets.
Office action dated Dec. 7, 2010 for U.S. Appl. No. 11/854,508, 17 sheets.
Current claims for U.S. Appl. No. 11/512,461 (6 sheets).
OA dated Oct. 1, 2008 for U.S. Appl. No. 11/512,461 (8 sheets).
OA dated May 22, 2009 for U.S. Appl. No. 11/512,461 (8 sheets).
OA dated Jan. 20, 2010 for U.S. Appl. No. 11/512,461 (9 sheets).
OA dated Aug. 2, 2010 for U.S. Appl. No. 11/512,461 (10 sheets).
OA dated Dec. 17, 2010 for U.S. Appl. No. 11/512,461 (2 sheets).
OA dated Jun. 21, 2011 for U.S. Appl. No. 11/512,461 (7 sheets).
Current claims for U.S. Appl. No. 11/854,508 (5 sheets).
OA dated Nov. 27, 2009 for U.S. Appl. No. 11/854,508 (13 sheets).
OA dated May 21, 2010 for U.S. Appl. No. 11/854,508 (15 sheets).
OA dated Dec. 7, 2010 for U.S. Appl. No. 11/854,508 (16 sheets).
OA dated May 25, 2011 for U.S. Appl. No. 11/854,508 (3 sheets).
OA dated Jan. 17, 2012 for U.S. Appl. No. 11/854,508 (13 sheets).

* cited by examiner

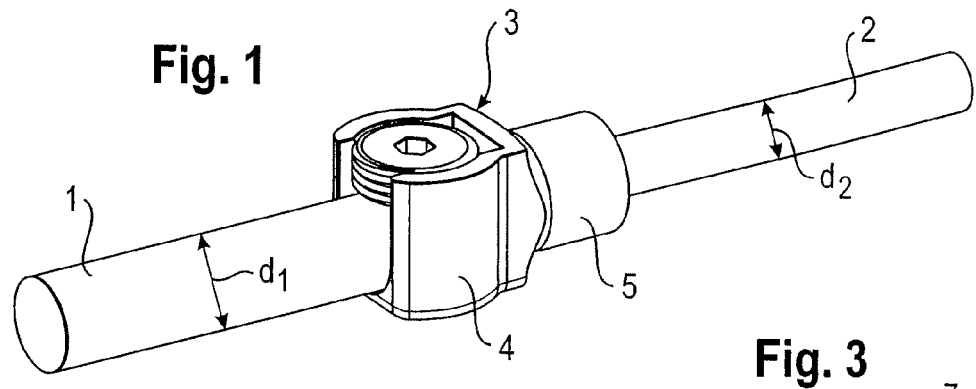
Fig. 1
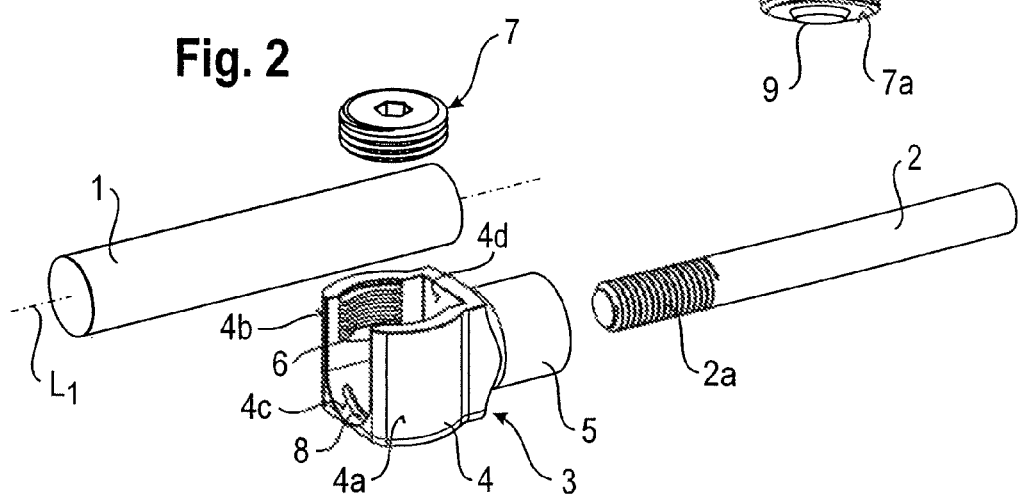
Fig. 2
Fig. 3
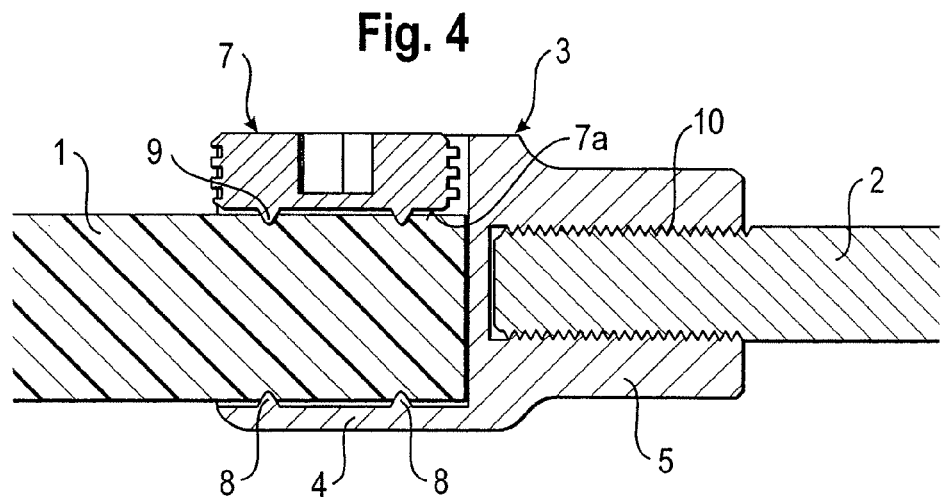
Fig. 4

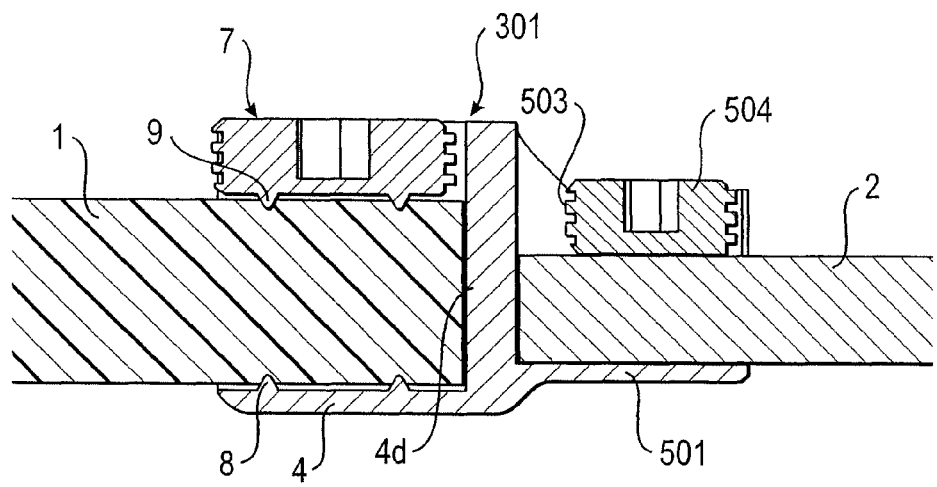
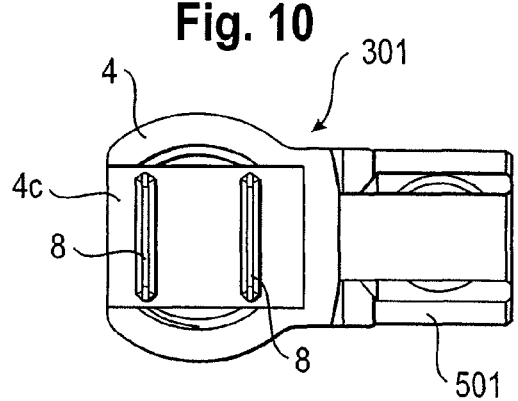
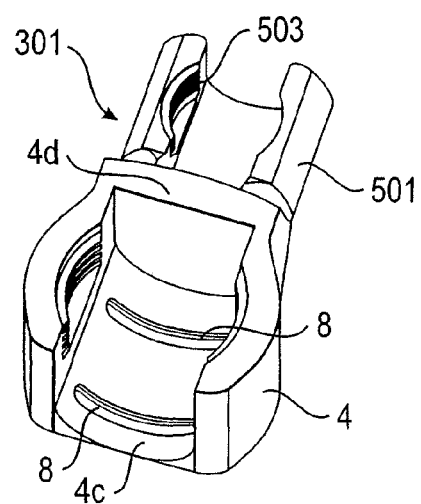

STABILIZATION DEVICE FOR STABILIZING BONES OF A VERTEBRA AND ROD CONNECTOR USED THEREFOR

CROSS-REFERENCE TO RELATED APPLICATION(S)

The present application claims the benefit of Provisional Patent Application Ser. No. 60/903,134, filed Feb. 23, 2007, and claims priority from European Patent Application EP 07003788.2, filed Feb. 23, 2007, the disclosures of which are incorporated herein by reference.

BACKGROUND

The invention relates to a stabilization device for stabilizing bones, and in particular to a stabilization device having a rod connector adapted to connect different types of rods, such as an elastic rod and a rigid rod.

Various devices for rigid fixation of portions of the spinal column are known. Generally, these devices comprise rigid spinal stabilization rods. It may be necessary to connect to different types of rigid rods. For example, WO 2005/099603 A1 discloses a spinal rod connector for connecting rigid rods.

For certain applications, a dynamic stabilization is desirable which allows a movement of the connected vertebrae to a specific degree. Also, a combination of rigid and dynamic stabilization of the spine may be appropriate in specific clinical situations. US 2007/0005063 A3 describes systems and methods for multi-level, multi-functional stabilization of a spinal column segment using motion preserving portions, which permit motion of at least a portion of a vertebral level, and motion preventing portions, that substantially prevent motion of at least a portion of an adjacent vertebral level.

Therefore, there is a need to provide a stabilization device which is versatile in use and simple in construction. In addition, there is a need for a rod connector that is suitable for connecting different types of rods, in particular flexible and rigid rods by which rigid rods and flexible rods can be used in combination for various clinical situations requiring rigid and/or dynamic stabilization.

SUMMARY OF THE INVENTION

A stabilization device according to the invention can be used, for example, at the end portion of a rigid fixation system that is used for the immobilization of a portion of the spinal column. In this case, the stabilization device acts as a protecting element to prevent overloading of the neighbouring motion segment.

In addition, a stabilization device according to the invention, can be used for a segmental stabilization with dynamic and rigid fixation in an alternating sequence.

In accordance with aspects of the invention, a rod connector can also be used to connect rigid rods only. Therefore the stabilization device is versatile in use.

In a specific embodiment, the rod connector can be connected to a bone anchor.

The rod connector is adapted to be used with a flexible rod, preferably made of an elastomer material, and with a rigid rod. When tightening the locking element to fix the flexible rod the deformation of the elastic material leads to an indirect or dynamic form-fit connection between the flexible rod, the rod connector and the locking element without harming the integral structure of the rod.

Furthermore, the fixation of the rods is achieved with a small number of parts. Therefore, the handling during surgery is facilitated.

Further features and advantageous of the invention will become apparent and will be best understood by reference by the following detailed description of embodiments taken in conjunction with the accompanying drawings.

BRIEF DESCRIPTION OF THE DRAWINGS

FIG. 1 shows a perspective view of the stabilization device according to a first embodiment.

FIG. 2 shows an exploded view of the stabilization device according to FIG. 1.

FIG. 3 shows a perspective view of the locking element of FIG. 2.

FIG. 4 shows an enlarged sectional view of the stabilization device.

FIG. 9 shows a sectional view of the stabilization device of FIG. 7.

FIG. 10 shows a top view of the rod connector of the stabilization device of FIG. 7.

FIG. 11 shows a perspective view from the top of the rod connector of the stabilization device according to FIG. 7.

DETAILED DESCRIPTION OF THE INVENTION

Figure 5:
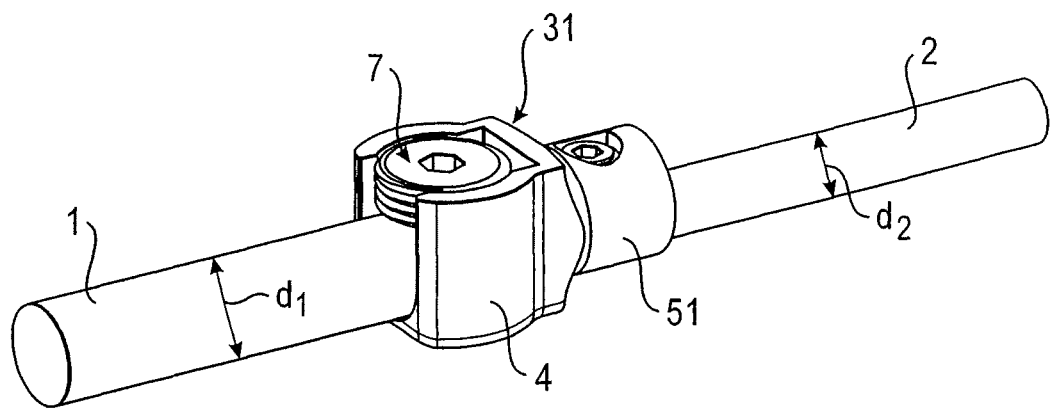
FIG. 5 shows a perspective view of a second embodiment of the stabilization device in an assembled state.

A first embodiment of the stabilization device is described with reference to FIGS. 1 to 4. The stabilization device comprises a first rod 1, a second rod 2 and a rod connector 3. The first rod 1 has, in the embodiment shown, a circular cross section with a diameter $d_1$. It is made of an elastic biocompatible material, preferably of plastics. For example, the rod can be made of an elastomer material in particular on the basis of polycarbonate-polyurethane, polycarbonateurethane (PCU) or polyether-polyurethane (PEU). The first rod exhibits elastic deformation under applied external loads. The surface of the first rod is preferably a smooth surface.

The second rod 2 has, in the embodiment shown, a circular cross section with a diameter $d_2$ which is smaller than the diameter $d_1$ of the first rod. The second rod 2 can be made of a rigid material such as a biocompatible metal or a metal alloy or of biocompatible plastics. The invention, however, is not limited to the embodiment wherein the first rod 1 and the second rod 2 are made of an elastic and a non-elastic material respectively and/or wherein the rods have a different diameter. The first rod can also be made of a rigid material. The cross section of the rods can have any shape. The diameters of the rods can be different or the same. Furthermore, the term rod is to be understood in the sense of an oblong member being adapted to span a distance between at least two vertebrae or at least two broken or injured bone portions.

The rod connector 3 is, in the embodiment shown, made of a single piece. It includes a first connection portion 4 for connection with the first rod 1 and a second connection portion 5 for connection with the second rod 2. The first connection portion 4 includes opposite side walls 4a, 4b, a side wall 4d connecting the opposite side walls 4a, 4b and a bottom wall connecting the side walls. The inner surface of the bottom wall forms a seat 4c for the first rod 1. The receiving portion formed by the walls has an approximately U-shaped cross section forming a channel for receiving the first rod 1. At the free end of the opposite side walls 4a, 4b an internal thread 6 is provided for receiving a locking element 7. The locking element 7 can be an inner screw which cooperates with the internal thread 6. The side wall 4d forms an abutting surface or a stop for the first rod 1 when the first rod 1 is inserted into the first connection portion.

As can be seen in particular in FIGS. 2 to 4 a plurality of rib-like projections 8 are provided on the surface of the seat 4c. The rib-like projections 8 extend in a direction perpendicular to the channel axis, i.e. when the rod 1 is inserted, perpendicular to the longitudinal axis $L_1$ of the first rod. In the embodiment shown, the projections 8 have a substantially triangular cross-section with a rounded tip. The projections 8 have such a length that they extend substantially across the seat. Each or several of the rib-like projections 8 may run out on one or an either side in groove like recesses providing depressions in the surface of the seat (not shown). The seat 4c forms a rod contacting surface. The projections form deviations in the rod contacting surface from the surface of the rod 1.

The inner screw 7 has at its rod contacting surface 7a a ring-shaped projection 9. The ring-shaped projection 9 forms an annular rib with a central cavity. The cross-section of the ring-shaped projection 9 is similar to the cross-section of rib-like projections 8 of the seat. The diameter of the ring-shaped projection in this embodiment corresponds to the distance of the two rib-like projections 8 which are formed on the seat. Hence, when the rod 1 is inserted into the first connection portion and the inner screw is screwed-in, the rib-like projections 8 and the portion of the ring-shaped projection 9 which contacts the rod are located on opposite sides of the rod. More specifically, the rib-like projections 8 and the portion of the ring-shaped projection 9 which contacts the rod engage the surface of the rod at diametrically opposed positions, respectively.

The second connection portion 5 is, in the embodiment shown, formed as cylindrical projection adjoining the side wall 4d. However, the outer shape of the second connection portion can have any other shape.

The second connection portion 5 comprises a bore 10, the diameter of which is sufficient to receive the second rod 2. The bore 10 can be threaded and the second rod 2 can have a threaded end portion 2a which cooperates with the internal thread of bore 10 to provide a threaded connection between second connection portion 5 and the second rod 2.

In use, the first rod 1 and the second rod 2 are connected in an arbitrary sequence with the rod connector 3. For example, first, the rod connector and the second rod 2 can be connected by screwing the end portion 2a into the bore 10. Thereafter, the first rod 1 is inserted into the receiving section of the first connection portion 4 until it rests on the seat 4c and abuts with its front face the rear side wall 4d. Thereafter, the inner screw 7 is inserted and tightened until the ring-shaped projection 9 comes into contact with the surface of the rod. As shown in FIG. 4 portions of the ring-shaped projection are pressed down on the surface of the rod. Similarly, the rib-like projections 8 are pressing on the surface of the rod from below. The projections do not harm the integrity of the surface of the rod. The rod begins to flow under the applied pressure. This material flow results in an indirect form-fit connection. The combination of direct frictional forces and indirect form-fit forces hold the rod in place. When the first rod 1 and the second rod 2 are both of a rigid material, the rods are fixed by frictional forces.

The free ends of the first rod and the second rod can be connected to further connectors or to bone anchors to anchor the stabilization device in the bone.

In a modification, the diameter of the ring-shaped projection 9 can be larger or smaller than the distance between the outmost rib-like projections 8. As in the embodiment shown, two rib-like projections 8 are provided. However, a plurality of rib-like projections can be provided. Similarly, a plurality of projections can be provided on the underside 7a of the inner screw. Also, a combination of projections and cavities can be provided on the underside of the locking element and the surface of the seat which would allow a material flow into the cavities.

In a further modification, the connection between the second rod 2 and the second connection portion is made by means of a press-fit connection.

Figure 6:
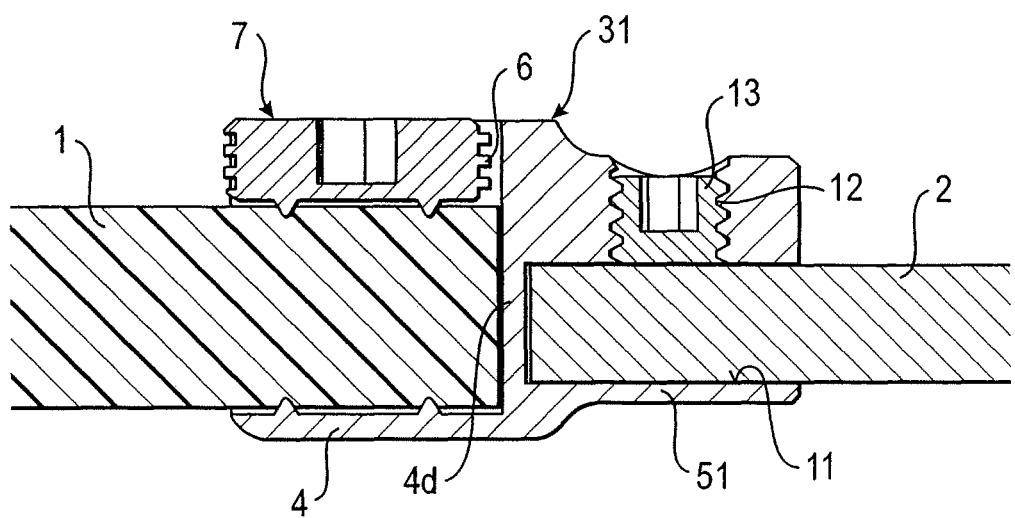
FIG. 6 shows a sectional view of the stabilization device of FIG. 5.
Figure 7:
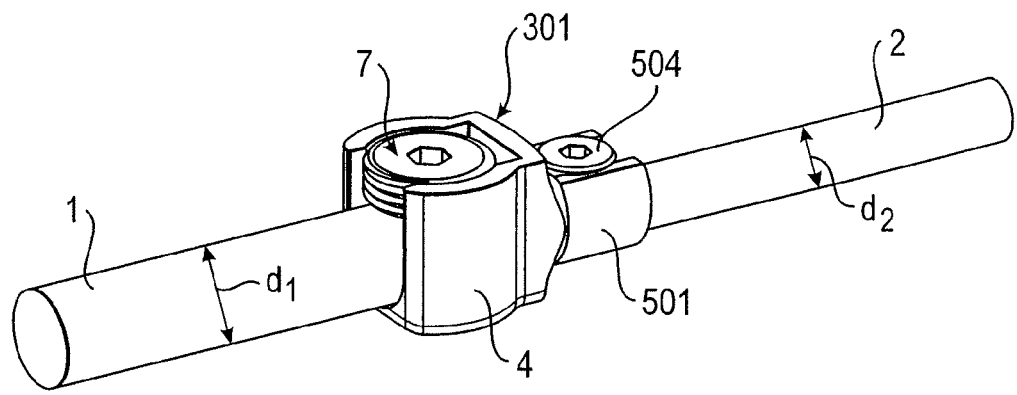
FIG. 7 shows a perspective view of a third embodiment of the stabilization device.
Figure 8:
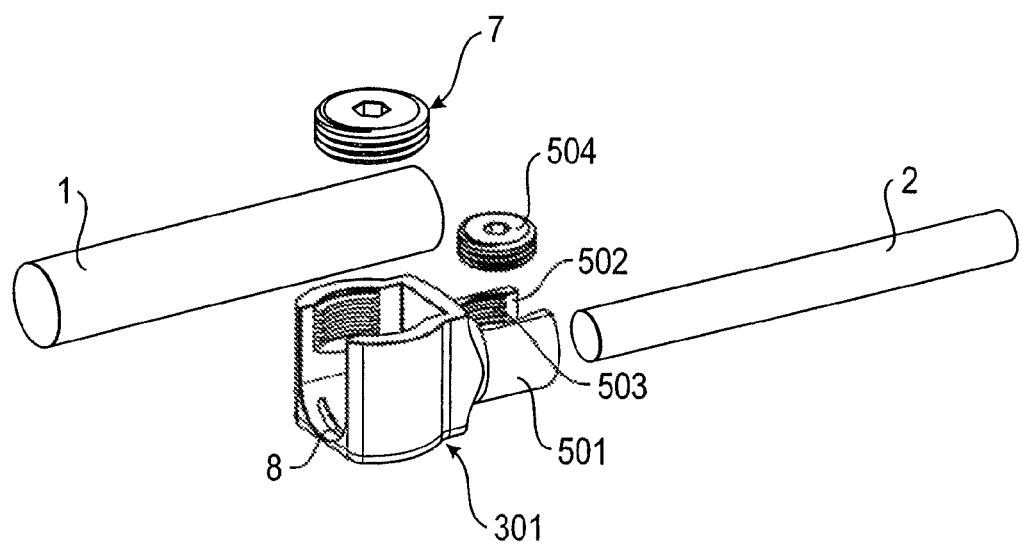
FIG. 8 shows an exploded perspective view of the stabilization device of FIG. 7.

FIGS. 5 and 6 show a second embodiment of the stabilization device. Parts which are the same as in the first embodiment are designated with the same reference numerals and the description thereof will not be repeated. The second embodiment differs from the first embodiment in the design of the rod connector 31. The rod connector 31 has the first connection portion 4 identical to the first embodiment. The second connection portion 51 includes a bore 11 the diameter of which is slightly larger than the diameter $d_2$ of the second rod 2 so that the second rod 2 can be introduced into the bore 11. Perpendicular to the bore 11 a threaded bore 12 is provided. An inner screw 13 can be screwed into the bore 12 for fixing the rod 2 in the bore 11 by means of clamping. The bore 12 extends in parallel to the internal thread 6. However, the bore 12 can be oriented in any way, for example at 90° around the longitudinal axis of the two rods relative to the orientation of the internal thread 6.

A third embodiment of the stabilization device is described with reference to FIGS. 7 to 11. Parts which are identical to the first embodiment are designated with the same reference numerals and the description thereof will not be repeated. The third embodiment differs from the first embodiment in the design of the rod connector. The rod connector 301 includes the first connection portion identical to the first embodiment but differs in the second connection portion. The second connection portion 501 comprises a substantially U-shaped recess 502 the width of which is slightly larger than the diameter $d_2$ of the second rod 2, so that the second rod 2 can be introduced into the recess 502. The U-shaped recess forms two open legs which have an internal thread 503 for receiving a locking element 504. The bottom of the U-shaped recess 502 which receives the rod 2 and the underside of locking element 504 which comes into contact with the rod 2 are smooth. Hence, if the rod 2 is made of a rigid material, which does not flow when an external load is applied, rod 2 is held in place by frictional forces. The side wall 4d forms an abutting surface for the rod 2 as well as for rod 1.

Figure 12:
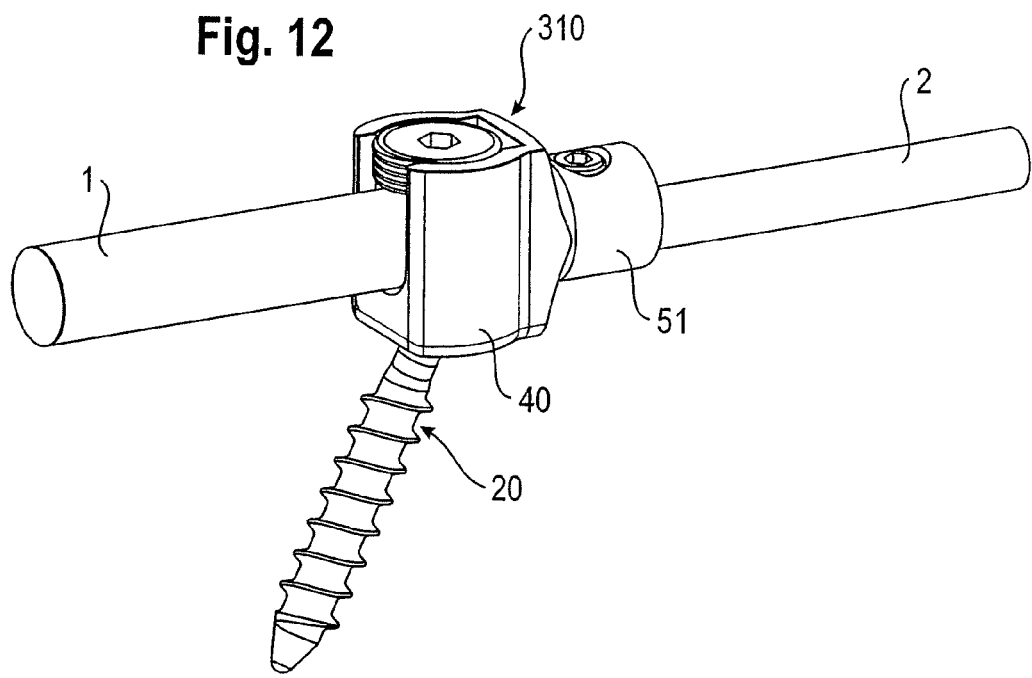
FIG. 12 shows a perspective view of a fourth embodiment of the stabilization device in an assembled state.
Figure 13:
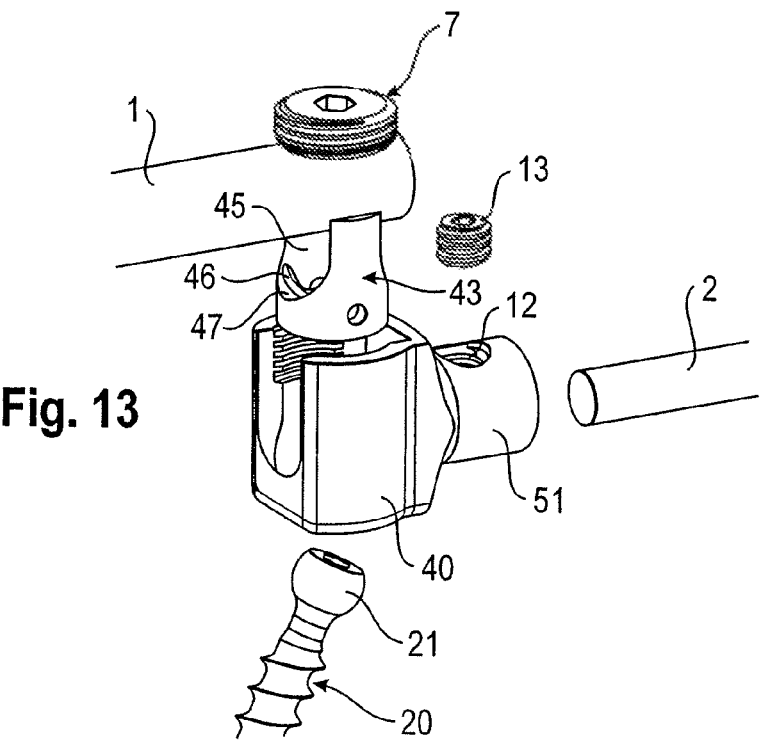
FIG. 13 shows an exploded view of the stabilization device of FIG. 12.
Figure 14:
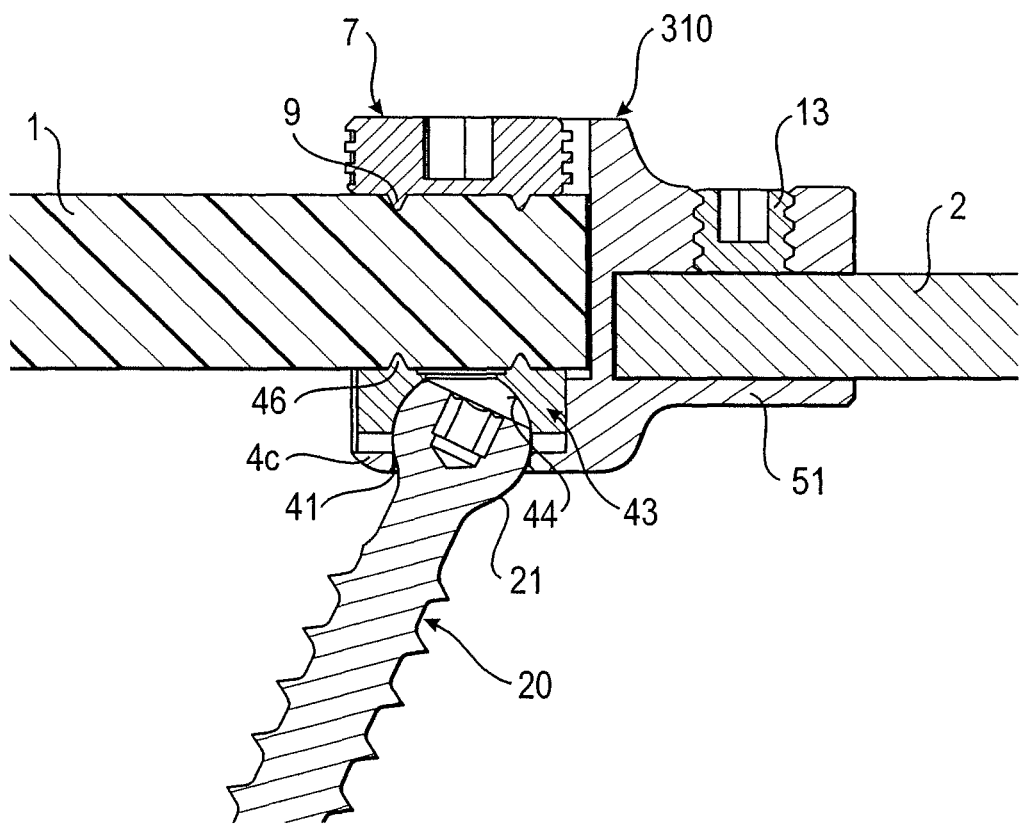
FIG. 14 shows a sectional view of the stabilization device of FIG. 12.

FIG. 12 to 14 show a fourth embodiment of the stabilization device. Parts which are the same as those of the previous described embodiments are designated with the same reference numerals and the description thereof will not be repeated.

The fourth embodiment differs from the previous embodiments in the design of the rod connector which allows a polyaxial connection with a bone anchor, for example a bone screw 20. The rod connector 310 as shown in FIGS. 12 to 14 includes a first connection portion 40 for connection with the first rod 1 and a second connection portion 5, which is in this example identical to the connection portion 5 shown in FIGS. 5 and 6. The first connection portion 40 comprises a bore 41 at the center of the seat. The shape of the bore 41 is preferably circular and the diameter of the bore 41 is smaller than the diameter of a spherical segment-shaped head 21 of the bone screw 20. The edge of the bore 41 can be shaped spherically or conically or otherwise shaped so that the bone screw 20 is pivotably held in first connection portion.

A pressure element 43 is provided, which has a substantially cylindrical shape so that it can be introduced into the receiving section of the first connection portion 40. The pressure element has on its side facing the head 21 a spherical recess 44 encompassing at least partly the head 21. Further, the pressure element 43 comprises a substantially U-shaped recess 45 forming a channel for receiving the rod 1. On the bottom 47 of the U-shaped recess 45 at least two rib-like projections 46 are provided, which are designed like the rib-like projections 8 according to the previous embodiments. The inner screw 7 is identical to the inner screw of the previous embodiments. Hence, the rod connector 310 differs in the first connection portion from the previous embodiments in that the seat for the rod 1 is provided in the pressure element 43. The pressure element is provided for exerting pressure onto the head 21 of the bone screw 20.

In use, the bone screw is introduced into the first connection section 40 of the rod connector 310, then the pressure element 43 is introduced. The bone screw 20, the pressure element 43 and rod connector 310 may be preassembled. When the bone screw 20 is screwed in a vertebra or a bone the rod connector 310 can be aligned to receive the rods due to the polyaxial connection between the bone screw 20 and the rod connector 310.

When the inner screw 7 is tightened, it may first press onto the first rod 1. However, after the first rod 1 is deformed due to its elasticity, the inner screw 7 contacts the flanges of the pressure element 43. Thus, the rod is locked in its position. Upon further tightening the inner screw 7, it presses onto the flanges of the pressure element 43. The pressure element 43 then exerts this pressure further onto the head which in turn is pressed against the edge of the bore 41. Thus, the bone screw is locked in its angular position.

In a further modification, the second connection portion is formed identical to the first connection portion so that it is possible to connect two rods of the same type, for example two elastic rods with each other.

Figure 15:
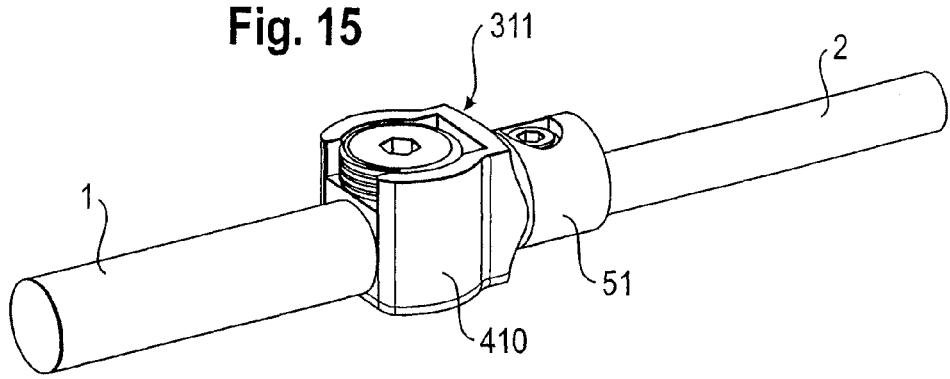
FIG. 15 shows a perspective view of a fifth embodiment of the stabilization device in an assembled state.
Figure 16:
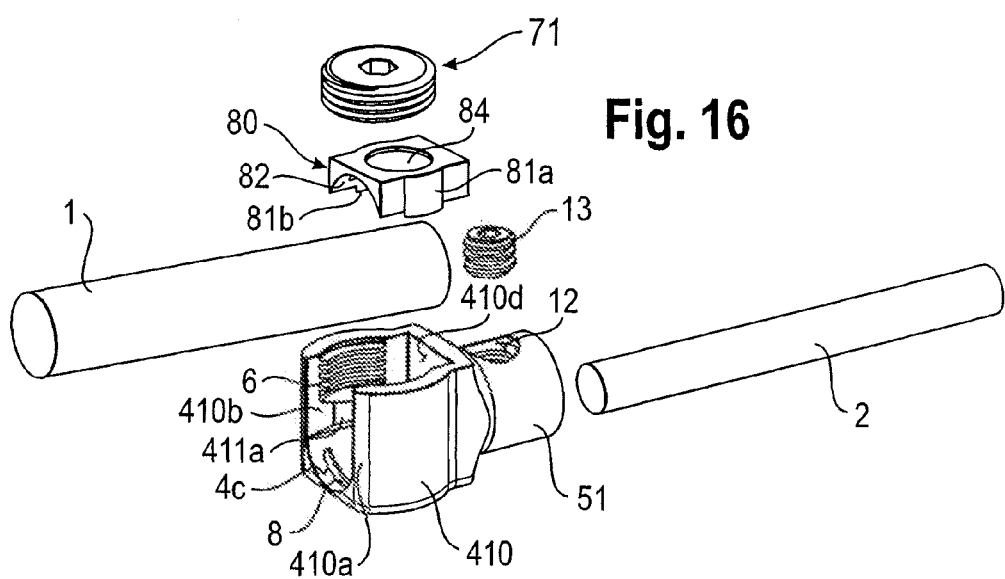
FIG. 16 shows an exploded view of the stabilization device of FIG. 15.
Figure 17:
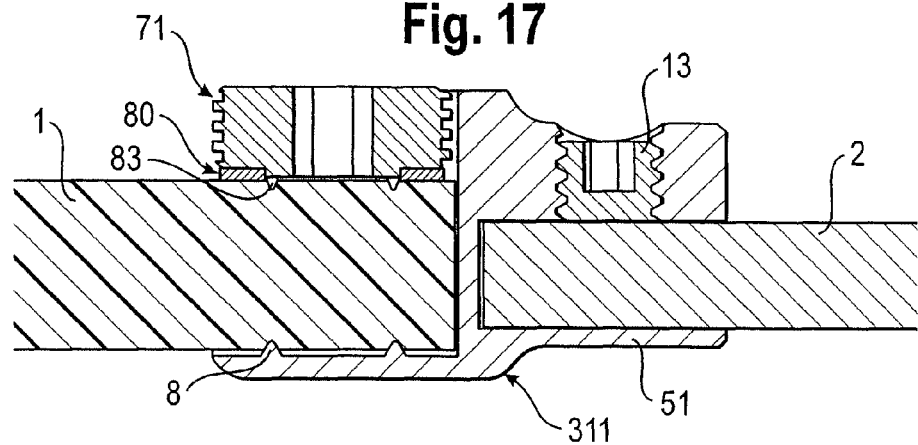
FIG. 17 shows a sectional view of the stabilization device of FIG. 15.

A fifth embodiment of the stabilization device is shown in FIGS. 15 to 17. Parts which are identical to the previous embodiments are indicated with the same reference numerals as in the previous embodiments. The stabilization device includes a rod connector 311 which differs from the rod connector of the previous embodiments in that a filling piece 80 is provided between the locking element 71 and the first rod 1. The connector 311 according to the fifth embodiment includes a first connection portion 410 which has opposite side walls 410a, 410b and a bottom wall 4c providing a seat for the rod 1 and which has projections 8 on the seat as in the previous embodiments. The side walls 410a and 410b have such a height that after insertion of the rod 1 a filling piece 80 can be introduced. On the inner wall of the side walls 410a, 410b beneath the internal thread 6 guiding grooves 411a, 411b can be provided which engage with guiding portions 81a, 81b which can be provided on the filling piece on opposite sides of the filling piece 80. The guiding grooves and the guiding portions can also be omitted. The filling piece 80 includes a recess 82 on its side facing the first rod 1 the shape of which is adapted to the outer shape of the rod. In the embodiment shown the recess 82 is a cylindrical segment-shaped recess 82. On the surface of the recess 82 which contacts the rod, rib-like projections 83 extending in a direction essentially perpendicular to the longitudinal axis of the rod 1 can be provided. On its opposite side the filling piece 80 can comprise an opening 84 into which a circular projection on the underside of the locking element 71 rotatably engages. The opening can also be omitted. The locking element 71 is similar to the locking element 7 of the previous embodiments. It can have a projection (not shown) engaging an opening 84 to provide a rotatable connection.

The second connection portion 51 is identical to that of the second embodiment. Between the first connection portion 410 and the second connection portion 51 a side wall 410d is provided which forms an abutting surface for the first and for the second rod when they are inserted.

In use, the filling piece is inserted after insertion of the first rod 1 and thereafter a locking element is screwed-in. The locking element is rotatable with respect to the filling piece. It presses onto the filling piece which in turn presses on the surface of the rod 1.

Figures 18A, 18B, 18C, 18D:
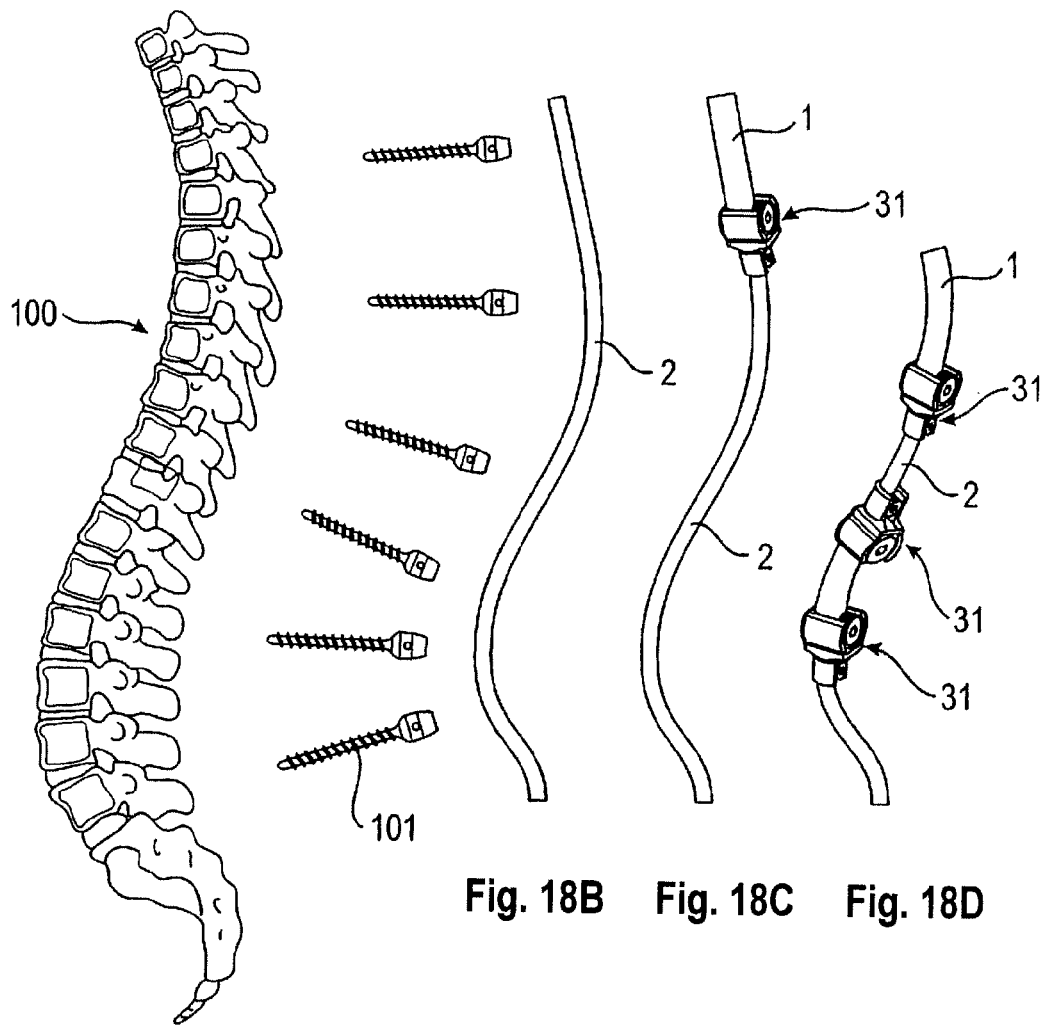
FIGS. 18A-D show schematic representations of applications of the stabilization device.

FIGS. 18A-D schematically shows different applications of the stabilization device with respect to a stabilization of the spinal column 100. FIG. 18A shows a spinal column 100 with bone anchors 101 which can be anchored in the vertebrae of the spinal column. FIG. 18B shows a single type of a rigid rod 2, for example a titanium rod, which can be connected with bone anchors 101 and anchored in the vertebrae of the spine for a rigid fixation. FIG. 18C shows at the end of a stabilization construct with a rigid rod 2, the connector 31 according to the invention which connects the end section of the rigid rod 2 with an elastic rod 1. In this case, the flow of forces can run out into the adjacent motion segment of the spine to protect it from overloading due to forces resulting from the rigid fixation of the stabilized motion segments.

FIG. 18D shows the application of the stabilization system in a construct where elastic rods 1 and rigid rods 2 are arranged in an alternating manner.

Other modifications are possible. For example, the first connection section and the second connection section can be located with respect to each other in such a way that the respective seats for the rods are at the same or at different heights so as to cope with different anatomical situations. Furthermore, the connection sections can be oriented with respect to each other at an angle which is different form zero degrees. The rod connector can be designed in such a way that the first and the second connection portion are provided in a side by side arrangement, i.e. opposing side walls of the first connection portion. The first and the second connection section may be formed as separate parts which could be connected to each other either permanently or detachably. The side wall 4d, 410d separating the first and the second connection portions can be omitted.

The elements of the various embodiments described can be combined, for example, each of the second connection portions can be combined with each of the first connection portions. The deviations from the contour of the rod surface which are provided on the rod contacting surface of the seat and/or locking element or the filling piece can have another shape than rib-like. For example point-like or spot-like projections/cavities can also be provided.

What is claimed is:

1. A stabilization device for stabilizing bones of a vertebra comprising:
   a first rod made of an elastic material;
   a second rod; and
   a rod connector configured to connect the first rod and the second rod, the rod connector comprising a first receiving portion for receiving the first rod and a first fixation element configured to cooperate with the first receiving portion to fix the first rod in the first receiving portion;
   wherein the first receiving portion comprises opposed side walls forming a generally U-shaped entry into the first receiving portion to receive the first rod therein, a bottom wall between the side walls forming a seat for the first rod, and an end wall between the side walls forming a stop to block movement of an end of the first rod when the first rod is seated between the side walls on the bottom wall;
   wherein in the first receiving portion a rod contacting surface is provided and wherein a contour of the rod contacting surface comprises deviations from a contour of a surface of the first rod;
   wherein the elastic material is configured to flow for a form-fit connection between the first rod and the contour of the rod contacting surface.

2. The stabilization device of claim 1, wherein the first rod is made of an elastomer material.

3. The stabilization device of claim 1, wherein the seat includes the deviations of the rod contacting surface.

4. The stabilization device of claim 1, wherein the second rod is a rigid rod.

5. The stabilization device of claim 1, wherein the deviations of the contour are at least one of projections and depressions.

6. The stabilization device of claim 1, wherein the first rod has a longitudinal axis and the deviations extend substantially in a direction transverse to the longitudinal axis of the first rod.

7. The stabilization device of claim 1, wherein the rod contacting surface comprises the seat for the first rod in the receiving portion and a clamping portion opposite to the seat, wherein the clamping portion is provided on the first fixation element.

8. The stabilization device of claim 1, wherein the rod contacting surface comprises the seat and a clamping portion opposite to the seat and wherein the clamping portion is provided on a filling piece arranged between the first fixation element and the first rod.

9. The stabilization device of claim 1, wherein the second rod and the rod connector are separate parts and the rod connector comprises a second receiving portion for receiving the second rod.

10. The stabilization device of claim 9, wherein the second receiving portion comprises an opening for receiving an end of the second rod therein and a second fixation element separate from the second rod and configured to cooperate with the second receiving portion to fix the second rod in the opening.

11. The stabilization device of claim 9, wherein the second receiving portion comprises an opening for receiving an end of the second rod therein, wherein the opening is a threaded bore and the end of the second rod has an external thread which cooperates with the thread of the threaded bore.

12. The stabilization device of claim 10 wherein the second receiving portion has a second opening to receive the second fixation element for fixing the second rod in the first opening.

13. The stabilization device of claim 12 wherein the second opening and the second fixation device are cooperatively threaded to permit fixing the second rod in the first opening.

14. The stabilization device of claim 10, wherein the opening is foamed by opposed side walls defining a generally U-shaped entry into the second receiving portion to receive the second rod therein, wherein said side walls of the U-shaped entry have an inner thread and the second fixation element is an inner screw to be screwed in said side walls of the U-shaped entry.

15. The stabilization device of claim 1, wherein the first rod is made of a plastic material.

16. The stabilization device of claim 1, wherein the first rod has a substantially uniform cross-section at least along a length of the end of the first rod.

17. A stabilization device for stabilizing bones of a vertebra comprising
   a first rod made of an elastic material;
   a second rod; and
   a rod connector configured to connect the first rod and the second rod, the rod connector comprising a first receiving portion for receiving the first rod, a first fixation element configured to cooperate with the first receiving portion to fix the first rod in the first receiving portion, a second receiving portion having an opening for receiving an end of the second rod therein, and a second fixation element for fixing the second rod in the opening, wherein the opening is a U-shaped recess with an inner thread and the second fixation element is an inner screw to be screwed in the U-shaped recess;
   wherein, in the first receiving portion, a rod contacting surface is provided and wherein a contour of the rod contacting surface comprises deviations from a contour of a surface of the first rod;
   wherein the elastic material of the first rod is configured to flow for a form-fit connection between the first rod and the contour of the rod contacting surface.

18. The stabilization device of claim 1, wherein the side walls of the U-shaped entry have an inner thread and the first fixation element is an inner screw to be screwed in the side walls of the U-shaped entry.

19. A stabilization device for stabilizing bones of a vertebra comprising
   a first rod made of an elastic material;
   a second rod;
   a bone anchor having a head and a shaft, and
   a rod connector configured to connect the first rod, the second rod and the bone anchor, the rod connector comprising a first receiving portion for receiving the first rod, a first fixation element configured to cooperate with the first receiving portion to fix the first rod in the first receiving portion, a second receiving portion having an opening for receiving an end of the second rod therein, and a third receiving portion for receiving the head of the bone anchor;
   wherein, in the first receiving portion, a rod contacting surface is provided and wherein a contour of the rod contacting surface comprises deviations from a contour of a surface of the first rod;
   wherein the elastic material of the first rod is configured to flow for a form-fit connection between the first rod and the contour of the rod contacting surface.

20. The stabilization device of claim 19 further comprising a pressure element for acting upon the head to fix the shaft at an angular position relative to the third receiving portion.

21. A rod connector for use in stabilizing bones of a vertebra comprising:
- a first receiving portion for receiving a first rod and a first fixation element configured to cooperate with the first receiving portion to fix the first rod in the first receiving portion, wherein the first receiving portion comprises opposed side walls forming a generally U-shaped entry into the first receiving portion to receive the first rod therein, a bottom wall between the side walls forming a seat for the first rod, and an end wall between the side walls forming a stop to block movement of an end of the first rod when the first rod is seated between the side walls on the bottom wall;
- a second receiving portion for receiving a second rod, the second receiving portion defining a first opening for receiving a second rod on an opposite side of the end wall from the seat for the first rod;
- wherein, in the first receiving portion, a rod contacting surface is provided and wherein a contour of the rod contacting surface comprises at least one of projections or depressions.

22. The rod connector of claim 21, wherein the first opening is a threaded bore to cooperate with a thread of a second rod.

23. The rod connector of claim 21, further comprising a second fixation element for fixing a second rod in the opening and wherein the first opening is a U-shaped recess with an inner thread and the second fixation element is an inner screw to be screwed in the U-shaped recess.

24. The rod connector of claim 21, further comprising a second fixation element, wherein the second receiving portion has a second opening to receive the second fixation element for fixing a second rod in the first opening.

25. The rod connector of claim 21, the rod connector further comprising a third receiving portion having bore that defines an edge to hold a head of a bone anchor;
- wherein, in the first receiving portion, a rod contacting surface is provided and wherein a contour of the rod contacting surface comprises deviations from a contour of a surface of the first rod;
- wherein the elastic material of the first rod is configured to flow for a form-fit connection between the first rod and the contour of the rod contacting surface.

* * * * *

UNITED STATES PATENT AND TRADEMARK OFFICE
CERTIFICATE OF CORRECTION

PATENT NO.        : 8,419,773 B2                          Page 1 of 1
APPLICATION NO.   : 12/035386
DATED             : April 16, 2013
INVENTOR(S)       : Lutz Biedermann et al.

It is certified that error appears in the above-identified patent and that said Letters Patent is hereby corrected as shown below:

In the Claims

Column 8, Claim 14, line 8          Delete "foamed"
                                    Insert -- formed --

Signed and Sealed this
Thirty-first Day of December, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,419,773 B2 | Page 1 of 1 |
| APPLICATION NO. | : 12/035386 | |
| DATED | : April 16, 2013 | |
| INVENTOR(S) | : Lutz Biedermann | |

It is certified that error appears in the above-identified patent and that said Letters Patent is hereby corrected as shown below:

On the Title Page

Item (73) Assignee          Delete "Bierdermann"

Insert -- Biedermann --

Signed and Sealed this

Eighteenth Day of March, 2014

Michelle K. Lee

*Deputy Director of the United States Patent and Trademark Office*